US012805715B2

(12) United States Patent
Elbaz et al.

(10) Patent No.: US 12,805,715 B2
(45) Date of Patent: Nov. 24, 2026

(54) LARYNGOSCOPE BLADE WITH LIGHT GUIDE

(71) Applicant: TELEFLEX LIFE SCIENCES LLC, Wilmington, DE (US)

(72) Inventors: Aviram Elbaz, Apex, NC (US); Vishal Temburni, Morrisville, NC (US); Alireza Sadritabrizi, Raleigh, NC (US)

(73) Assignee: TELEFLEX LIFE SCIENCES LLC, Wilmington, DE (US)

(*) Notice: Subject to any disclaimer, the term of this patent is extended or adjusted under 35 U.S.C. 154(b) by 841 days.

(21) Appl. No.: 17/160,296

(22) Filed: Jan. 27, 2021

(65) Prior Publication Data

US 2021/0145268 A1 May 20, 2021

Related U.S. Application Data

(63) Continuation of application No. PCT/US2019/044016, filed on Jul. 30, 2019.

(Continued)

(51) Int. Cl.

*A61B 1/267* (2006.01)
*A61B 1/06* (2006.01)
*A61B 1/07* (2006.01)

(52) U.S. Cl.

CPC ............ *A61B 1/267* (2013.01); *A61B 1/0669* (2013.01); *A61B 1/07* (2013.01); *A61B 1/0684* (2013.01)

(58) Field of Classification Search

CPC ..... A61B 1/267; A61B 1/2673; A61B 1/2676; A61B 1/07; A61B 1/0669; A61B 1/0676; A61B 1/0684

See application file for complete search history.

(56) References Cited

U.S. PATENT DOCUMENTS

| | | | |
|---|---|---|---|
| 1,785,343 | A | 12/1930 | Gilbert |
| 2,289,226 | A | 7/1942 | Von Foregger |

(Continued)

FOREIGN PATENT DOCUMENTS

| | | | |
|---|---|---|---|
| CN | 1031318 | A | 3/1989 |
| DE | 2621232 | | 11/1977 |

(Continued)

OTHER PUBLICATIONS

Hilbro brochure, Green System Fiber Optic Laryngoscope, Interchangeable Light Guide Insert, Oct. 2001.

(Continued)

*Primary Examiner* — Eduardo C Robert
*Assistant Examiner* — Anna V. Little
(74) *Attorney, Agent, or Firm* — BakerHostetler

(57) ABSTRACT

A laryngoscope blade is provided for insertion into a patient's airway. The laryngoscope blade includes a spatula having a top surface, a proximal region, a distal region, and a longitudinal centerline extending from the proximal region to the distal region. A connector base is provided at the proximal end of the spatula for coupling the blade to a laryngoscope handle. A light guide has a first end attached to the connector base by a resilient fastener, and a second end capable of illuminating the patient's airway. A housing is provided adjacent the top surface of the spatula and includes space for receiving a portion of the light guide. The second end of the light guide has a longitudinal axis oriented substantially parallel to the longitudinal centerline of the spatula such that light emitted from the second end of the light guide is oriented directly toward a tip of the spatula.

20 Claims, 12 Drawing Sheets

Related U.S. Application Data

(60) Provisional application No. 62/711,859, filed on Jul. 30, 2018.

(56) References Cited

U.S. PATENT DOCUMENTS

| | | | | | |
|---|---|---|---|---|---|
| 2,433,705 | A | | 12/1947 | Palmeter | |
| 2,630,114 | A | | 3/1953 | Hart | |
| 2,646,036 | A | | 7/1953 | Allyn | |
| 2,854,004 | A | | 9/1958 | Durrant | |
| 2,911,968 | A | | 11/1959 | Schueler | |
| 3,426,749 | A | | 2/1969 | Jephcott | |
| 3,507,272 | A | | 4/1970 | Laerdal | |
| 3,595,222 | A | | 7/1971 | Vellacott | |
| 3,598,113 | A | | 8/1971 | Moore | |
| 3,638,644 | A | | 2/1972 | Reick | |
| 3,766,909 | A | | 10/1973 | Ozbey | |
| 3,771,514 | A | | 11/1973 | Huffman et al. | |
| 3,779,655 | A | | 12/1973 | Toyota | |
| 3,826,248 | A | | 7/1974 | Gobels | |
| 3,856,001 | A | | 12/1974 | Phillips | |
| 3,986,854 | A | | 10/1976 | Scrivo et al. | |
| 4,037,588 | A | | 7/1977 | Heckele | |
| 4,112,933 | A | | 9/1978 | Moses | |
| 4,124,939 | A | | 11/1978 | Onoue | |
| 4,126,127 | A | | 11/1978 | May | |
| 4,273,112 | A | | 6/1981 | Heine et al. | |
| 4,295,465 | A | * | 10/1981 | Racz | A61B 1/267 600/199 |
| 4,337,761 | A | | 7/1982 | Upsher | |
| 4,360,008 | A | | 11/1982 | Corazzelli, Jr. | |
| 4,406,280 | A | | 9/1983 | Upsher | |
| 4,425,709 | A | | 1/1984 | Quenzi | |
| 4,437,458 | A | | 3/1984 | Upsher | |
| 4,488,655 | A | | 12/1984 | Itsubo et al. | |
| 4,519,514 | A | | 5/1985 | Agbay et al. | |
| 4,527,553 | A | | 7/1985 | Upsher | |
| 4,556,052 | A | | 12/1985 | Muller | |
| 4,557,256 | A | | 12/1985 | Bauman | |
| 4,565,187 | A | | 1/1986 | Soloway | |
| 4,570,614 | A | * | 2/1986 | Bauman | A61B 1/267 600/199 |
| 4,579,108 | A | | 4/1986 | Bauman | |
| 4,583,527 | A | | 4/1986 | Musicant et al. | |
| 4,596,239 | A | | 6/1986 | Bauman | |
| 4,669,449 | A | | 6/1987 | Bauman | |
| 4,679,547 | A | | 7/1987 | Bauman | |
| 4,694,822 | A | | 9/1987 | Bauman | |
| 4,694,969 | A | | 9/1987 | Granat | |
| 4,862,772 | A | | 9/1989 | Piperato | |
| 4,878,486 | A | | 11/1989 | Slater | |
| 4,884,558 | A | | 12/1989 | Gorski et al. | |
| 4,924,855 | A | | 5/1990 | Salerno et al. | |
| 4,930,495 | A | | 6/1990 | Upsher | |
| 4,958,624 | A | | 9/1990 | Stone et al. | |
| 4,972,825 | A | | 11/1990 | Vescovo, Jr. | |
| 4,996,976 | A | | 3/1991 | Nakagawa | |
| 5,003,962 | A | * | 4/1991 | Choi | A61B 1/267 600/199 |
| 5,036,835 | A | | 8/1991 | Filli | |
| 5,038,766 | A | | 8/1991 | Parker | |
| 5,060,633 | A | * | 10/1991 | Gibson | A61B 1/267 600/199 |
| 5,065,738 | A | | 11/1991 | Van Dam | |
| 5,095,624 | A | | 3/1992 | Ennis | |
| 5,169,257 | A | | 12/1992 | Liou | |
| 5,178,131 | A | | 1/1993 | Upsher | |
| D337,384 | S | | 7/1993 | Schucman | |
| 5,305,932 | A | | 4/1994 | Iseli | |
| 5,355,870 | A | | 10/1994 | Lacy | |
| 5,443,058 | A | | 8/1995 | Ough | |
| 5,501,651 | A | | 3/1996 | Bauman | |
| 5,529,570 | A | * | 6/1996 | Storz | A61B 1/267 600/199 |
| 5,575,758 | A | | 11/1996 | Easterbrook, III | |
| 5,651,760 | A | | 7/1997 | Upsher | |
| 5,678,718 | A | | 10/1997 | Morris et al. | |
| 5,685,079 | A | | 11/1997 | Brothers et al. | |
| 5,702,351 | A | | 12/1997 | Bar-Or et al. | |
| 5,727,682 | A | | 3/1998 | Abidin et al. | |
| 5,769,094 | A | | 6/1998 | Jenkins, Jr. et al. | |
| 5,776,053 | A | * | 7/1998 | Dragisic | A61B 1/267 600/195 |
| D399,957 | S | | 10/1998 | Chernov et al. | |
| 5,873,818 | A | | 2/1999 | Rothfels | |
| 5,879,304 | A | | 3/1999 | Shuchman et al. | |
| D413,977 | S | | 9/1999 | Cranton et al. | |
| 5,984,863 | A | | 11/1999 | Ansari | |
| 6,013,026 | A | | 1/2000 | Krauter et al. | |
| 6,102,851 | A | | 8/2000 | Mellin | |
| 6,123,666 | A | | 9/2000 | Wrenn et al. | |
| 6,139,491 | A | | 10/2000 | Heine et al. | |
| 6,213,937 | B1 | | 4/2001 | Vivenzio | |
| 6,248,061 | B1 | | 6/2001 | Cook, Jr. | |
| 6,354,993 | B1 | | 3/2002 | Kaplan et al. | |
| 6,394,295 | B2 | | 5/2002 | Claude | |
| 6,471,643 | B1 | * | 10/2002 | Henderson | A61B 1/267 600/185 |
| 6,626,829 | B1 | | 9/2003 | Skaggs | |
| 6,666,819 | B2 | | 12/2003 | Heine et al. | |
| 6,719,688 | B2 | * | 4/2004 | Pecherer | A61B 1/267 600/199 |
| 6,735,825 | B1 | | 5/2004 | Berman et al. | |
| 6,890,298 | B2 | | 5/2005 | Berci et al. | |
| 6,918,184 | B2 | | 7/2005 | Glesser | |
| 6,964,637 | B2 | | 11/2005 | Dalle et al. | |
| D512,778 | S | | 12/2005 | Ashraf | |
| 7,007,392 | B2 | | 3/2006 | Ping | |
| 7,039,975 | B1 | | 5/2006 | Liao | |
| 7,044,909 | B2 | | 5/2006 | Berci et al. | |
| 7,128,710 | B1 | * | 10/2006 | Cranton | A61B 1/267 600/199 |
| 7,214,184 | B2 | | 5/2007 | McMorrow | |
| D544,601 | S | | 6/2007 | Iqbal | |
| D554,255 | S | | 10/2007 | Iqbal | |
| D559,982 | S | | 1/2008 | Iqbal | |
| D562,452 | S | | 2/2008 | Iqbal | |
| 7,338,440 | B1 | | 3/2008 | Smith | |
| D581,532 | S | | 11/2008 | Cranton et al. | |
| 7,608,040 | B1 | | 10/2009 | Dunst | |
| 7,611,459 | B2 | | 11/2009 | Geist et al. | |
| D609,808 | S | | 2/2010 | Tenger et al. | |
| 7,736,304 | B2 | | 6/2010 | Pecherer | |
| 7,771,350 | B2 | | 8/2010 | Geist et al. | |
| 7,824,331 | B1 | | 11/2010 | Cranton et al. | |
| D628,693 | S | | 12/2010 | Thuenker | |
| D629,516 | S | | 12/2010 | Firmin | |
| D629,517 | S | | 12/2010 | Jauch et al. | |
| D630,735 | S | | 1/2011 | Behrbohm | |
| D630,738 | S | | 1/2011 | Tenger et al. | |
| D630,739 | S | | 1/2011 | Tenger et al. | |
| D630,744 | S | | 1/2011 | Tenger et al. | |
| D631,156 | S | | 1/2011 | Halder et al. | |
| D631,158 | S | | 1/2011 | Doerges | |
| D632,783 | S | | 2/2011 | Maesarapu | |
| 7,878,973 | B2 | | 2/2011 | Yee et al. | |
| D634,008 | S | | 3/2011 | Tenger et al. | |
| 7,909,758 | B2 | | 3/2011 | Shapiro | |
| 7,909,759 | B2 | | 3/2011 | Pecherer | |
| D643,921 | S | | 8/2011 | Davila | |
| D645,146 | S | | 9/2011 | Lee | |
| 8,142,353 | B2 | | 3/2012 | Pecherer et al. | |
| 8,162,826 | B2 | | 4/2012 | Pecherer et al. | |
| D659,246 | S | | 5/2012 | McGrath et al. | |
| 8,251,898 | B2 | | 8/2012 | Pecherer | |
| 8,267,856 | B2 | | 9/2012 | Anders | |
| D669,680 | S | | 10/2012 | Goldstein | |
| 8,337,402 | B1 | * | 12/2012 | Ellis | A61B 1/267 600/199 |
| 8,414,481 | B2 | | 4/2013 | Hakanen et al. | |
| 8,512,234 | B2 | | 8/2013 | Grey et al. | |
| 8,628,879 | B2 | | 1/2014 | Pecherer et al. | |
| 8,702,598 | B2 | * | 4/2014 | Geist | A61B 1/00101 600/199 |

(56) References Cited

U.S. PATENT DOCUMENTS

| | | | | |
|---|---|---|---|---|
| 8,715,171 | B2 | 5/2014 | Pastron | |
| 8,979,745 | B2 | 3/2015 | Swift | |
| 8,998,804 | B2 | 4/2015 | Boedeker | |
| 9,078,614 | B2 | 7/2015 | Bird | |
| D738,501 | S | 9/2015 | Renner | |
| D739,017 | S | 9/2015 | Renner | |
| 9,173,545 | B2 * | 11/2015 | Schoonbaert | A61B 1/00052 |
| D745,669 | S | 12/2015 | Swift | |
| D746,451 | S | 12/2015 | Chen | |
| 9,198,567 | B1 | 12/2015 | Dube | |
| D748,255 | S | 1/2016 | McGrath et al. | |
| 9,314,151 | B2 | 4/2016 | McGrath et al. | |
| 9,320,420 | B2 * | 4/2016 | Goldstein | A61B 1/267 |
| 9,357,904 | B2 | 6/2016 | Wu | |
| 9,414,743 | B2 | 8/2016 | McGrath | |
| 9,510,745 | B2 | 12/2016 | Geist et al. | |
| 9,622,651 | B2 * | 4/2017 | Miller | A61B 1/00009 |
| 9,662,001 | B2 | 5/2017 | McGrath et al. | |
| D791,943 | S | 7/2017 | Cook | |
| 9,737,202 | B2 | 8/2017 | McGrath | |
| 10,244,922 | B2 | 4/2019 | Elbaz et al. | |
| D862,696 | S | 10/2019 | Elbaz et al. | |
| D863,555 | S | 10/2019 | Elbaz et al. | |
| 10,588,498 | B2 | 3/2020 | Dan et al. | |
| 2001/0014768 | A1 | 8/2001 | Kaplan et al. | |
| 2002/0068854 | A1 * | 6/2002 | Heine | A61B 1/267 600/199 |
| 2002/0082477 | A1 | 6/2002 | Kim | |
| 2002/0082478 | A1 | 6/2002 | McGrath | |
| 2002/0087050 | A1 | 7/2002 | Rudischhauser et al. | |
| 2003/0088156 | A1 * | 5/2003 | Berci | A61B 1/042 600/199 |
| 2003/0092967 | A1 | 5/2003 | Fourie et al. | |
| 2003/0120131 | A1 | 6/2003 | Pecherer et al. | |
| 2004/0034281 | A1 | 2/2004 | Cartledge et al. | |
| 2004/0122292 | A1 | 6/2004 | Dey et al. | |
| 2004/0127770 | A1 | 7/2004 | McGrath | |
| 2004/0129741 | A1 | 7/2004 | Stoneberg et al. | |
| 2004/0215062 | A1 | 10/2004 | Dalle et al. | |
| 2005/0043590 | A1 | 2/2005 | Mazzei et al. | |
| 2005/0090712 | A1 | 4/2005 | Cubb | |
| 2005/0234303 | A1 | 10/2005 | McMorrow | |
| 2005/0240081 | A1 | 10/2005 | Eliachar | |
| 2006/0079734 | A1 | 4/2006 | Miyagi | |
| 2006/0100483 | A1 | 5/2006 | Sundet et al. | |
| 2006/0189847 | A1 | 8/2006 | Yee et al. | |
| 2007/0093693 | A1 | 4/2007 | Geist et al. | |
| 2007/0112257 | A1 * | 5/2007 | Hensler | A61B 1/0684 600/199 |
| 2007/0129606 | A1 | 6/2007 | Pecherer | |
| 2007/0129607 | A1 | 6/2007 | Ashfaque | |
| 2007/0161863 | A1 | 7/2007 | Bentt | |
| 2007/0167686 | A1 | 7/2007 | McGrath | |
| 2007/0179342 | A1 | 8/2007 | Miller et al. | |
| 2007/0197873 | A1 | 8/2007 | Birnkrant | |
| 2008/0004498 | A1 * | 1/2008 | Pecherer | A61B 1/00032 600/193 |
| 2008/0045801 | A1 | 2/2008 | Shalman et al. | |
| 2008/0051628 | A1 | 2/2008 | Pecherer et al. | |
| 2008/0096099 | A1 | 4/2008 | Pecherer et al. | |
| 2008/0188717 | A1 | 8/2008 | Chen et al. | |
| 2008/0234549 | A1 * | 9/2008 | Geist | A61B 1/267 600/194 |
| 2008/0300464 | A1 | 12/2008 | Dhingra et al. | |
| 2009/0065007 | A1 | 3/2009 | Wilkinson et al. | |
| 2009/0099421 | A1 | 4/2009 | Shalman et al. | |
| 2009/0112067 | A1 | 4/2009 | Baker | |
| 2009/0187078 | A1 * | 7/2009 | Dunlop | A61B 1/07 600/179 |
| 2009/0209816 | A1 | 8/2009 | Gunther Nielsen et al. | |
| 2009/0270684 | A1 * | 10/2009 | Nielsen | A61B 1/00062 600/193 |
| 2009/0318767 | A1 | 12/2009 | Tenger et al. | |
| 2010/0004514 | A1 | 1/2010 | Shalman et al. | |
| 2010/0022843 | A1 | 1/2010 | Pecherer et al. | |
| 2010/0036204 | A1 | 2/2010 | Anders | |
| 2010/0041953 | A1 | 2/2010 | Pecherer et al. | |
| 2010/0191062 | A1 | 7/2010 | Kieffer | |
| 2010/0198017 | A1 | 8/2010 | Raspallo | |
| 2010/0217085 | A1 | 8/2010 | Williams et al. | |
| 2010/0258563 | A1 | 10/2010 | Parrinello et al. | |
| 2010/0261968 | A1 | 10/2010 | Nearman et al. | |
| 2011/0060190 | A1 | 3/2011 | Pecherer | |
| 2011/0077466 | A1 | 3/2011 | Rosenthal | |
| 2011/0245609 | A1 | 10/2011 | Laser | |
| 2012/0055470 | A1 | 3/2012 | Pecherer et al. | |
| 2013/0018227 | A1 | 1/2013 | Schoonbaert | |
| 2014/0202459 | A1 * | 7/2014 | Iqbal | A61M 16/0488 128/200.26 |
| 2014/0371536 | A1 | 12/2014 | Miller et al. | |
| 2015/0112146 | A1 * | 4/2015 | Donaldson | A61B 1/00048 600/188 |
| 2016/0000305 | A1 | 1/2016 | Elbaz et al. | |
| 2016/0220106 | A1 * | 8/2016 | Pecherer | A61B 1/00066 |
| 2016/0317005 | A1 | 11/2016 | Dunlop | |
| 2016/0317008 | A1 | 11/2016 | McGrath et al. | |
| 2017/0020384 | A1 | 1/2017 | Fitzgerald et al. | |
| 2017/0079518 | A1 | 3/2017 | Elbaz et al. | |
| 2017/0150878 | A1 * | 6/2017 | Swift | A61B 1/00032 |
| 2017/0202447 | A1 | 7/2017 | Pecherer | |

FOREIGN PATENT DOCUMENTS

| | | | | | |
|---|---|---|---|---|---|
| DE | 20218560 | | | 5/2003 | |
| DE | 102011018688 | | | 10/2012 | |
| EP | 0184588 | | | 6/1986 | |
| EP | 0653180 | | | 10/1998 | |
| EP | 2255721 | A1 | * | 12/2010 | A61B 1/00052 |
| GB | 685741 | | | 1/1953 | |
| GB | 806467 | | | 12/1958 | |
| GB | 2102294 | A | * | 2/1983 | A61B 1/267 |
| GB | 2102679 | A | | 2/1983 | |
| GB | 2385793 | | | 9/2003 | |
| GB | 2491189 | | | 11/2012 | |
| GB | 2537118 | A | * | 10/2016 | A61B 1/267 |
| JP | 02-052630 | A | | 2/1990 | |
| JP | 07-051217 | A | | 2/1995 | |
| JP | 2013-526324 | A | | 6/2013 | |
| WO | 83/01373 | | | 4/1983 | |
| WO | WO-8301373 | A1 | * | 4/1983 | A61B 1/267 |
| WO | 88/00021 | | | 1/1988 | |
| WO | 99/44490 | | | 9/1999 | |
| WO | WO-9944490 | A1 | * | 9/1999 | A61B 1/267 |
| WO | 2005/082231 | | | 9/2005 | |
| WO | 2005/107575 | | | 11/2005 | |
| WO | 2006/131770 | | | 12/2006 | |
| WO | 2009/066078 | | | 5/2009 | |
| WO | WO-2014035730 | A1 | * | 3/2014 | A61B 1/00126 |
| WO | 2016/092134 | | | 6/2016 | |
| WO | 2018/023138 | | | 2/2018 | |
| WO | 2020/050922 | | | 3/2020 | |

OTHER PUBLICATIONS

Medizintechnik KaWe Germany, Laryngoscopes Catalog, Megalight F.O.

Flexicare BitePro Solo product webpage (https://www.flexicare.com/products/airway-management/single-use-laryngos-copes/britepro-solo).

International Search Report for PCT/US2019/044016, mailed Mar. 31, 2020.

* cited by examiner

LARYNGOSCOPE BLADE WITH LIGHT GUIDE

CROSS-REFERENCE TO RELATED APPLICATIONS

This application is a continuation of International Patent Application PCT/US2019/044016, filed Jul. 30, 2019, which claims priority to U.S. Provisional Patent Application No. 62/711,859, filed Jul. 30, 2018, the contents of which are incorporated herein by reference in their entirety.

FIELD OF THE DISCLOSURE

The present disclosure relates generally to a laryngoscope blade for use with a laryngoscope handle, and more particularly, to a laryngoscope blade having a light guide to illuminate a patient's airway.

BACKGROUND

A laryngoscope is a type of device for assisting in the observation of the oral cavity, particularly the laryngeal areas. This device is frequently employed to aid in the placement of a tube into the larynx of a patient. In order to obtain accurate placement, the laryngoscope must be capable of restraining the patient's tongue, while engaging the epiglottis to reveal the larynx for visual observation. The laryngoscope is also useful for general examination of the larynx. Commonly, a primary function of a laryngoscope is to expose the larynx in order to facilitate the insertion of an endotracheal tube.

The surface of the laryngoscope blade adjacent the handle is urged against the tongue and mandible to expose the larynx in such procedures, and the opposite blade surface is positioned opposing the upper front teeth of the patient. For instance, the surface of the blade adjacent to the handle is used to press against the tongue and mandible of a patient in a supine position, in order to prevent the patient's tongue from obstructing the visual examination of the larynx. These functions are greatly aided by the use of a light guide used in association with the laryngoscope blade to produce localized illumination of the area to be examined.

Many conventional laryngoscopes have a number of drawbacks and deficiencies. For instance, in conventional laryngoscopes, a proximal end of the light guide is coupled to a light source in a handle and a distal end of the light guide is configured to illuminate a portion of the blade. However, a portion of the light guide is typically bent in order to achieve this arrangement, thus degrading the intensity of light emitted from the distal end of the light guide. Moreover, in conventional laryngoscopes, a portion of the blade, such as a tip of the blade, may only be partially illuminated due to the orientation of the distal end of the light guide. Thus, conventional laryngoscopes typically have a small or limited area of illumination. Additionally, in conventional laryngoscopes, the placement of the light guide relative to the blade typically obstructs the practitioner's field of view during use, as well as interferes with an endotracheal tube during intubation. Further, in conventional laryngoscopes, the light guide is often fully exposed, and thus the light guide is susceptible to contamination or damage during use. Exposed portions of the light guide, or parts of the blade that secure the light guide, may also be harmful to the patient during use since they could cause trauma to the patient during insertion.

The present disclosure solves these aforementioned problems, amongst others. Such a laryngoscope of the present disclosure is therefore operable for use in situations where the intensity and direction of light emitted from the light guide is a critical factor in allowing doctors to carry out successful intubation in the minimum amount of time and without harm to the patient.

SUMMARY OF THE DISCLOSURE

The foregoing needs are met, to a great extent, by the present disclosure, in which a laryngoscope blade is configured to be inserted into a patient's airway, the laryngoscope blade comprising: a spatula having a top surface, a proximal region, a distal region, and a longitudinal centerline extending from the proximal region to the distal region; a connector base provided at the proximal end of the spatula and configured to removably couple the laryngoscope blade to a laryngoscope handle; a light guide having a first end and a second end, the first end attached to the connector base by a resilient fastener, and the second end configured to illuminate the patient's airway; and a light guide housing adjacent the top surface of the spatula, the light guide housing having a side wall defining a space configured to receive a portion of the light guide; the second end of the light guide having a longitudinal axis oriented substantially parallel to the longitudinal centerline of the spatula such that light emitted from the second end of the light guide is oriented directly toward a tip of the spatula.

In another aspect, the light guide housing has a stepped configuration including a side wall extending generally vertically from the top surface of the spatula, and a top wall extending laterally from an edge of the side wall.

In another aspect, the side wall, a first portion of the top wall, and a portion of the top surface of the spatula cooperate to define a cavity configured to receive and retain a portion of the light guide in a secure position.

In another aspect, the laryngoscope further comprises a cover removably attached to the housing and configured to seal the cavity for protecting the portion of the light guide retained therein.

In another aspect, the cover is configured to be removably snap-fitted onto a portion of the laryngoscope blade to prevent access to the portion of the light guide retained within the housing.

In another aspect, the cover includes snap-fit lugs configured to fit in and engage corresponding mounting holes located within the cavity.

In another aspect, the cover further includes a flexible tab configured to engage the housing to maintain the cover in a position securely mounted over the cavity.

In another aspect, the side wall of the housing and the top surface of the spatula cooperate to form a longitudinal channel configured to enable a practitioner to see along the length of the blade and thus into the patient's larynx, and also to provide a passage for intubation of an endotracheal tube.

In another aspect, the light guide housing further includes an end wall having an opening defining a light guide passage through which the distal end of the light guide extends for providing illumination to the distal region of the spatula.

In another aspect, the laryngoscope further comprises a retaining wall extending from the top surface of the spatula at the distal region and connected to both the end wall and a second portion of the top wall.

In another aspect, the end wall has an outlet opening in which the distal end of the light guide passes through.

In another aspect, the end wall, the outlet opening, and the retainer wall are configured to position the distal end of the light guide to extend straight toward the distal region of the spatula in a direction parallel to the longitudinal axis of the spatula in order to illuminate an oropharyngeal space during laryngoscopy or during an intubation procedure.

In another aspect, the light guide housing has a sidewall extending from a longitudinal edge of the spatula and defining a semi-circular cross-sectional channel configured to stably receive and retain a portion of the light guide therein.

In another aspect, the light guide housing further includes a retainer wall extending from the spatula at the distal region and has a semi-circular cross section configured to receive and retain a distal end of the light guide.

In another aspect, the laryngoscope further comprises an outlet opening disposed between the oppositely oriented side wall and the retainer wall and arranged such that the distal end of the light guide extends therethrough and is oriented to illuminate the distal region of the spatula such that a longitudinal axis of the distal end of the light guide is substantially parallel to the longitudinal centerline of the laryngoscope spatula.

In another aspect, the connector base includes a rear heel portion and a front claw portion configured to detachably engage a portion of a laryngoscope handle.

In another aspect, the light guide is configured to fit within the housing and extends from the distal region of the blade to the proximal region of the blade and to a bottom of the heel portion.

In another aspect, the laryngoscope further comprises an annular elastomeric fastener configured to fittingly and securely receive the proximal end of the light guide therein.

In another aspect, the fastener includes a lip that extends from a bottom surface of the heel portion so that the proximal end of the light guide likewise extends from the bottom surface of the heel portion.

In another aspect, the lip portion of the fastener has a frustoconical shape.

There has thus been outlined certain embodiments of the disclosure in order that the detailed description thereof herein may be better understood, and in order that the present contribution to the art may be better appreciated. There are additional embodiments of the disclosure that will be described below and which form the subject matter of the claims appended hereto.

In this respect, before explaining at least one embodiment of the disclosure in detail, it is to be understood that the disclosure is not limited in its application to the details of construction and to the arrangements of the components set forth in the following description or illustrated in the drawings. The disclosure is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

DETAILED DESCRIPTION

Figure 1:
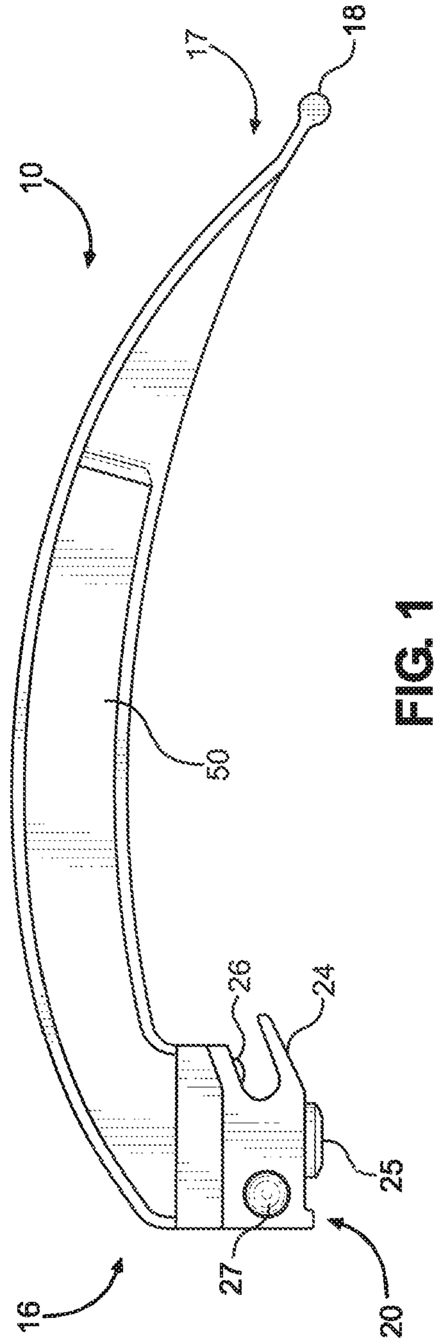
FIG. 1 is a left side elevation view illustrating a laryngoscope blade in accordance with an implementation of the present disclosure.
Figure 2:
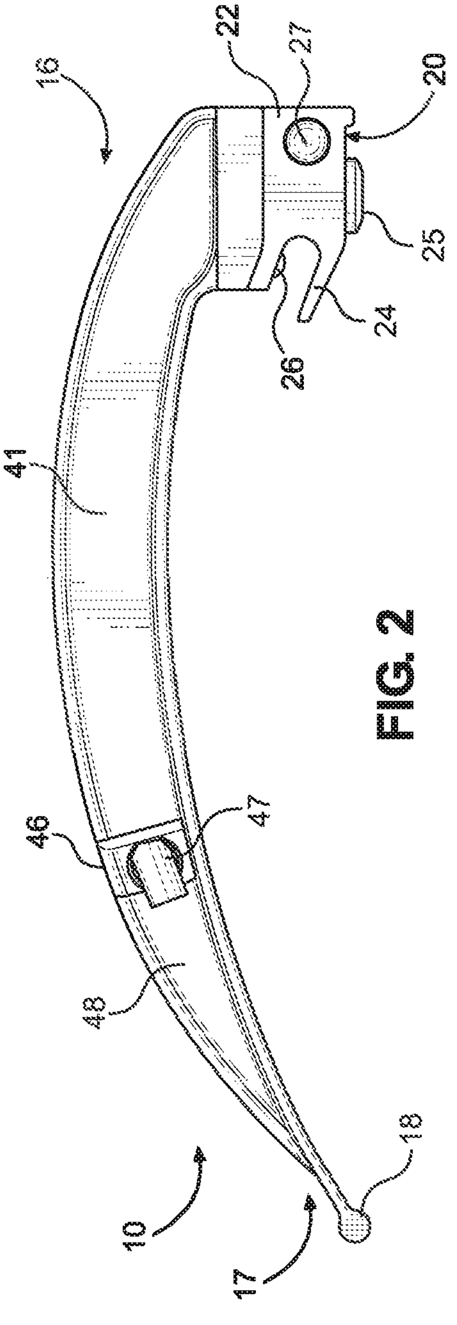
FIG. 2 is a right-side elevation view illustrating the laryngoscope blade of FIG. 1.
Figure 4:
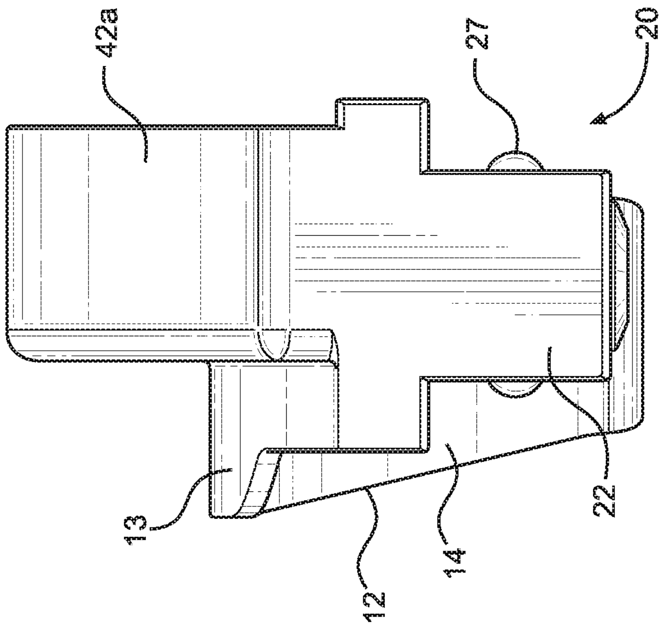
FIG. 4 is a rear elevation view illustrating the laryngoscope blade of FIG. 1.
Figure 3:
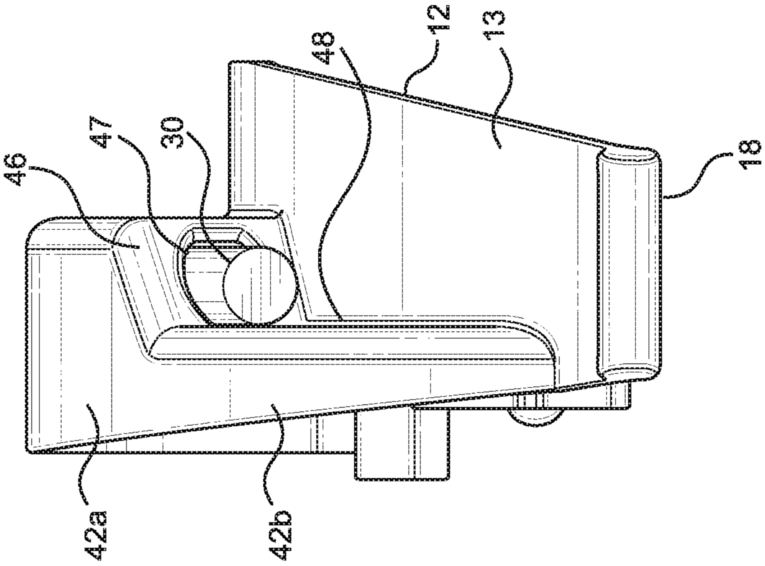
FIG. 3 is a front elevation view illustrating the laryngoscope blade of FIG. 1.
Figure 5:
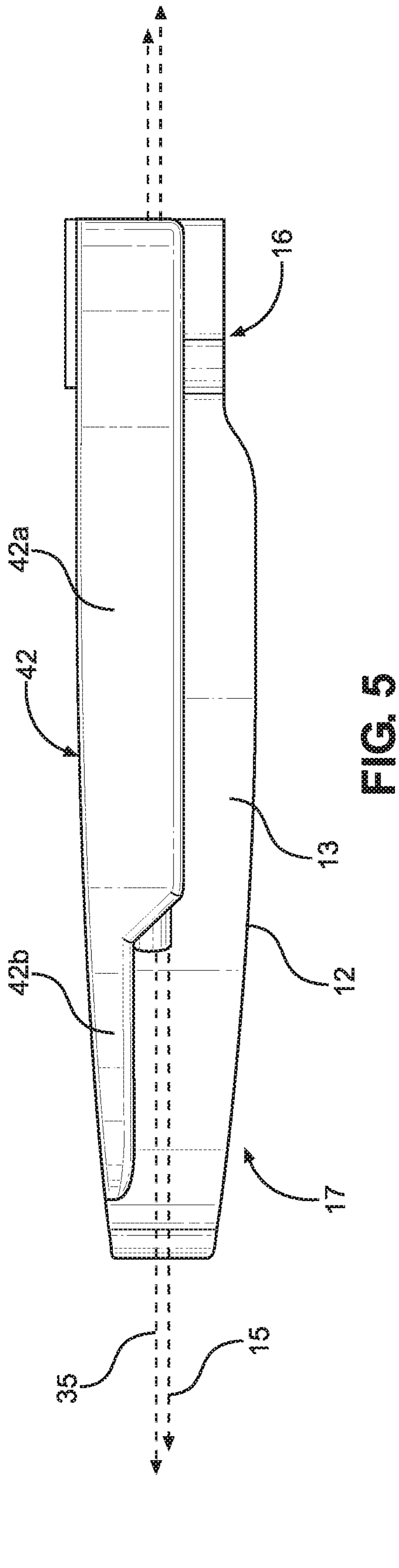
FIG. 5 is a top plan view illustrating the laryngoscope blade of FIG. 1.
Figure 6:
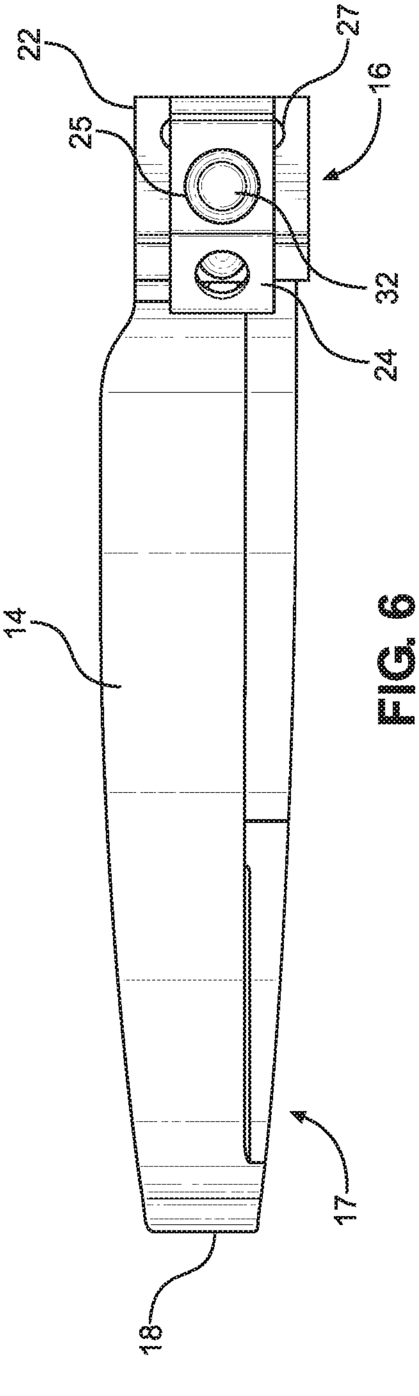
FIG. 6 is a bottom plan view illustrating the laryngoscope blade of FIG. 1.
Figure 7:
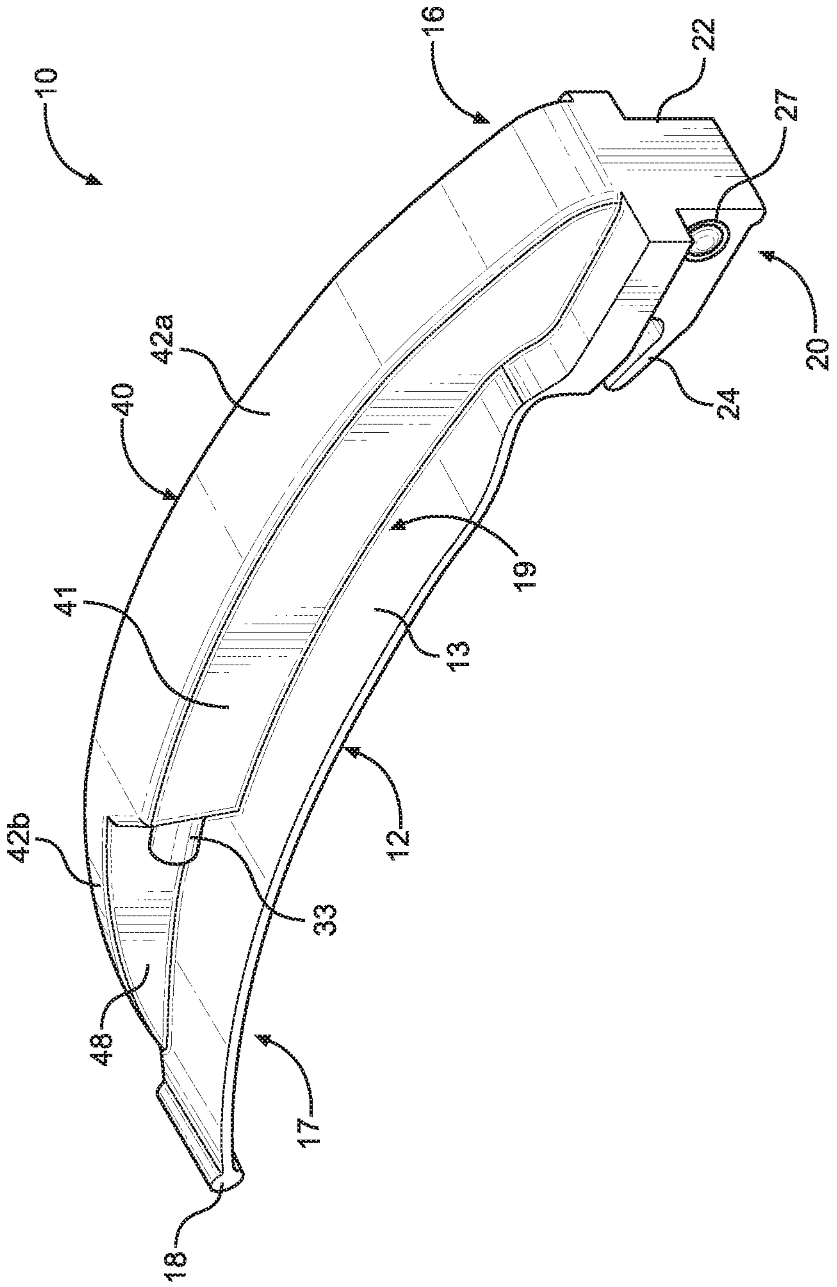
FIG. 7 is a rear perspective view illustrating the laryngoscope blade of FIG. 1.
Figure 8:
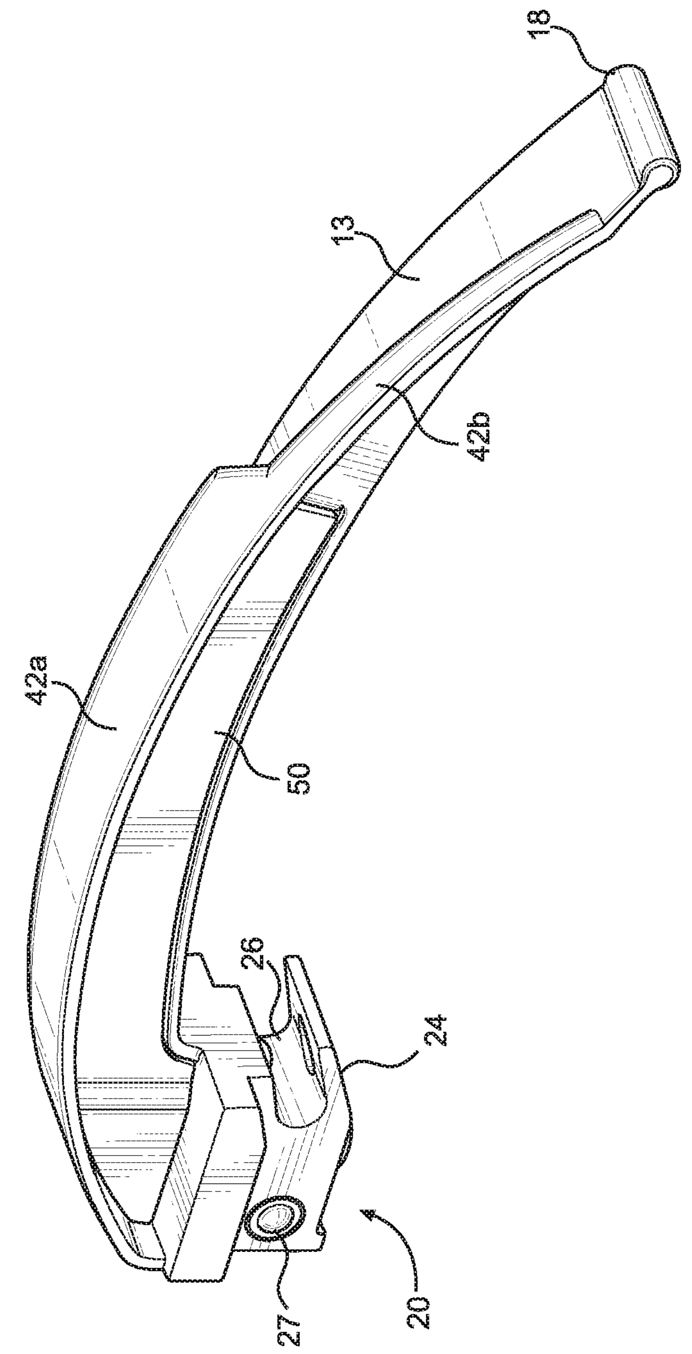
FIG. 8 is a front perspective view illustrating the laryngoscope blade of FIG. 1.
Figure 9:
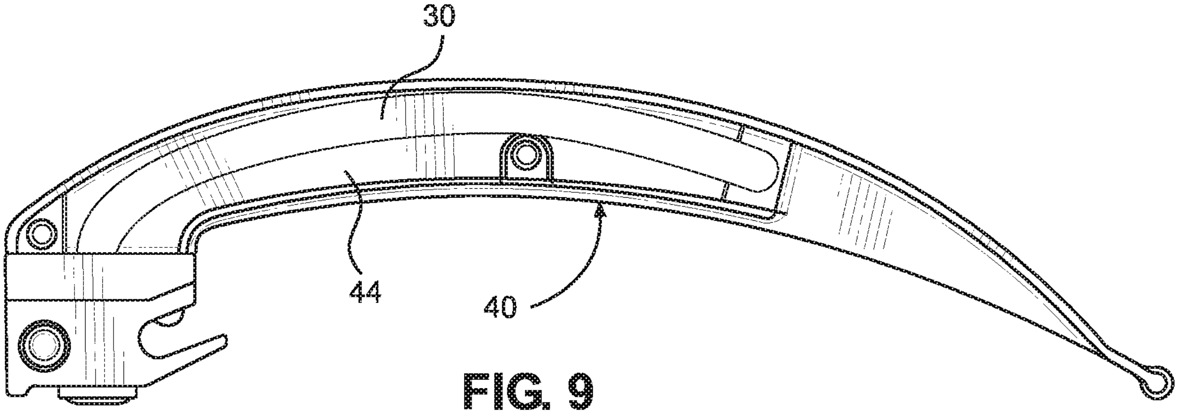
FIG. 9 is a side elevation view of the laryngoscope blade of FIG. 1 without a snap-on cover.
Figure 10:
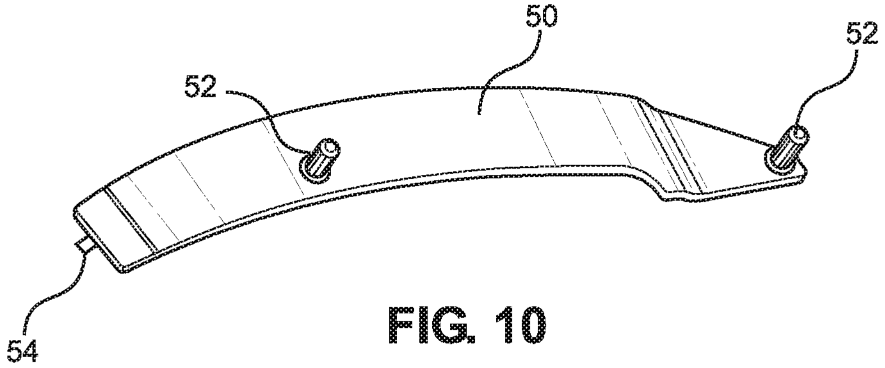
FIG. 10 is a perspective view of a snap-cover for the laryngoscope blade of FIG. 1.

The disclosure will now be described with reference to the drawing figures, in which like parts are referred to with like reference numerals throughout. One or more embodiments in accordance with the present disclosure provide a laryngoscope blade configured to be inserted into a patient's airway passage. The laryngoscope blade is further configured to be removably attached to a laryngoscope handle (not shown) to form an operative generally L-shaped configuration for assisting intubation.

In particular, FIGS. 1-11 illustrate an implementation of a generally curved type of laryngoscope blade 10 according to the present disclosure. The laryngoscope blade 10 may be made from metal, plastic, or a combination thereof. For instance, the blade 10 may be made from austenitic stainless steel, or may be molded from a biocompatible plastic. Further, the laryngoscope blade 10 may be a single-use design to prevent potential contamination between uses. The laryngoscope blade 10 includes a laryngoscope spatula 12 having a top surface 13 and a bottom surface 14. The laryngoscope spatula 12 further has a longitudinal centerline

15 and a proximal region 16 and a distal region 17 correspondingly adjacent to and remote from the laryngoscope handle in the operative generally L-shaped configuration. The distal region 17 of the spatula 12 terminates in a tip 18 having a rounded edge to prevent or minimize trauma to a patient during insertion into the patient's airway passage.

The laryngoscope blade 10 also includes an illumination arrangement for providing illumination at the distal region 17 of the spatula 12 when in the operative configuration. The illumination arrangement includes a handle mounted illumination source, such as a bulb, and a blade mounted light guide 30, such as a polymer-based flexible carrier tube having a fiber optic cable, or a bundle of fiber optic cables, disposed therein for transmitting the illumination light from the illumination source to the distal region 17 of the spatula. More specifically, the light guide 30 includes a proximal end 32 configured to communicate with the illumination source, and a distal end 33 configured to illuminate the distal region 17 of the spatula 12 to assist visual inspection of the larynx or esophagus of the patient. It should be appreciated that various types of light sources may be incorporated within the lighting system. For example, the light source may be mounted within the handle and may include a light emitting diode (LED), a halogen bulb, a krypton bulb, and/or a xenon bulb, among others. In some implementations, the light source may be located in the laryngoscope blade. A power source, such as a battery, for powering the illumination source may be provided within the handle.

The proximal region 16 of the laryngoscope blade 10 includes a connector base 20 having a snap fit arrangement for detachably engaging the laryngoscope blade 10 with the laryngoscope handle. The laryngoscope handle may be reusable and includes a grippable housing which is configured to retain the source of electrical power, such as the battery, and the source of light, such as the bulb. The light and power sources are configured to be actuated upon contact of a portion of the laryngoscope blade with a conductor on a securable mounting end at the upper end of the handle surrounding the bulb.

A light guide housing 40 is connected to the spatula 12. In particular, the light guide housing 40 has a stepped configuration including a side wall 41 extending generally vertically from the top surface 13 of the spatula, and a top wall 42 extending laterally from an edge of the side wall 41 and having a contour that approximates a contour of the spatula 12. The top wall 42 may form a curved flange extending from the proximal region 16 of the blade toward the distal region 17. The side wall 41 and a first portion **42*a* of the top wall 42, along with a portion of the top surface 13 of the spatula 12, define a cavity 44 configured to receive and retain a portion of the light guide 30 in a secure position. As will be discussed in further detail below, a cover 50 may be removably attached to the housing to seal the cavity 44 for protecting the portion of the light guide 30 retained therein, i.e., to protect it from damage and/or make it less susceptible to contamination. The side wall 41 of the housing 40 and the top surface 13 of the spatula 12 also cooperate to form a longitudinal channel 19** configured to enable a practitioner to see along the length of the blade and thus into a patient's larynx, and also to provide a passage for intubation of an endotracheal tube.

The light guide housing 40 further includes an end wall 46 having an opening 47 defining a light guide passage through which the distal end 33 of the light guide 30 may extend in order to provide illumination to the distal region 17 of the blade 10. A retaining wall 48 extends from the top surface 13 of the spatula at the distal region 17 and is connected to both the end wall 46 and a second portion **42*b* of the top wall 42. The retaining wall 48 and the second portion 42*b* of the top wall 42 define a curved distal shell portion. The end wall 46 faces in the distal direction and has an outlet opening 47 in which the light guide 24 is arranged, such that the distal end 33 of the light guide 30 can emerge through the outlet opening. In particular, the end wall 46 is obliquely disposed between and connected to both the side wall 41 and the retainer wall 48. The first portion 42*a* of the top wall and the second portion 42*b* of the top wall form a continuous surface. As shown for example in FIG. 5, the end wall 46, the outlet opening 47, and the retainer wall 48 are configured to position the distal end 33 of the light guide 30 to extend straight toward the distal region 17 of the spatula 12, and more particularly, to extend straight toward the blade tip 18 in a direction parallel to the longitudinal axis of the spatula. Specifically, a longitudinal axis 35 of the light guide 30 at its distal end 33 is substantially parallel to the longitudinal centerline 15 of the laryngoscope spatula 12 in order illuminate a region directly straight ahead. Accordingly, when the laryngoscope 10 is in use, it is thus possible to illuminate the oropharyngeal space during laryngoscopy or also during an intubation procedure. Further, the light guide 30 is centered relative to a lengthwise direction of the connector base 20 such that the light guide does not laterally bend to conform with a surface of the blade. As a result, the intensity of light emitted from the distal end of the light guide 30** is not degraded. Further, this arrangement provides a better field of view for the practitioner over conventional light guides that laterally bend toward a direction across a surface of the blade and which therefore obscure the practitioner's field of view.

The cover 50 may be arranged to be removably snap-fitted onto a portion of the laryngoscope body so as to prevent access to the portion of the light guide 30 retained within the housing 40. In particular, the snap-on cover 50 is located over the cavity 44 and includes snap fit lugs 52 configured to fit in and engage corresponding mounting holes located within the cavity. Once fitted to blade 10, the lugs 52 prevent subsequent removal of snap on cover 50. The arrangement of the lugs 52 may also act as a guide for securely retaining the light guide 30 in a predetermined position. In other words, the location of the lugs 52 and corresponding mounting holes direct the shape of the light guide 30 within the cavity 44 so that the light guide is not overly bent in order to prevent degradation of light intensity emitted from its distal end, and also to maintain the distal end of the light guide pointing in the predetermined forward direction toward the tip of the blade without laterally bending the light guide. Further, the cover 50 may also include a flexible tab 54 configured to act as a catch with the housing for keeping the cover 50 securely mounted over the cavity.

Figure 11:
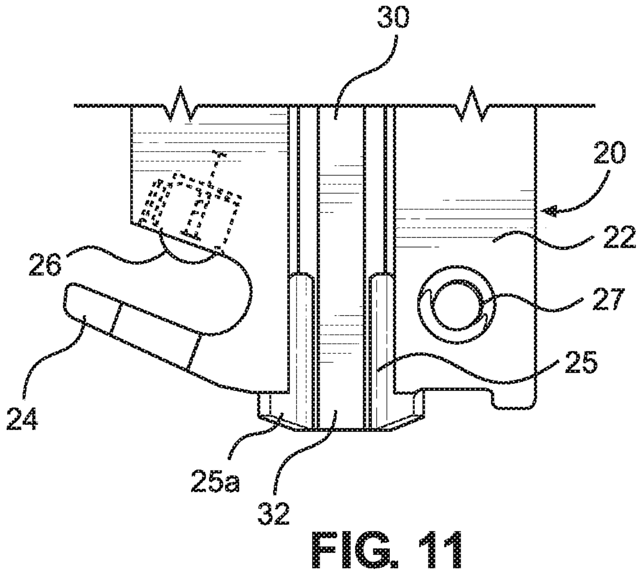
FIG. 11 is a partial cross-sectional view of a connector base of the laryngoscope blade of FIG. 1.
Figure 12:
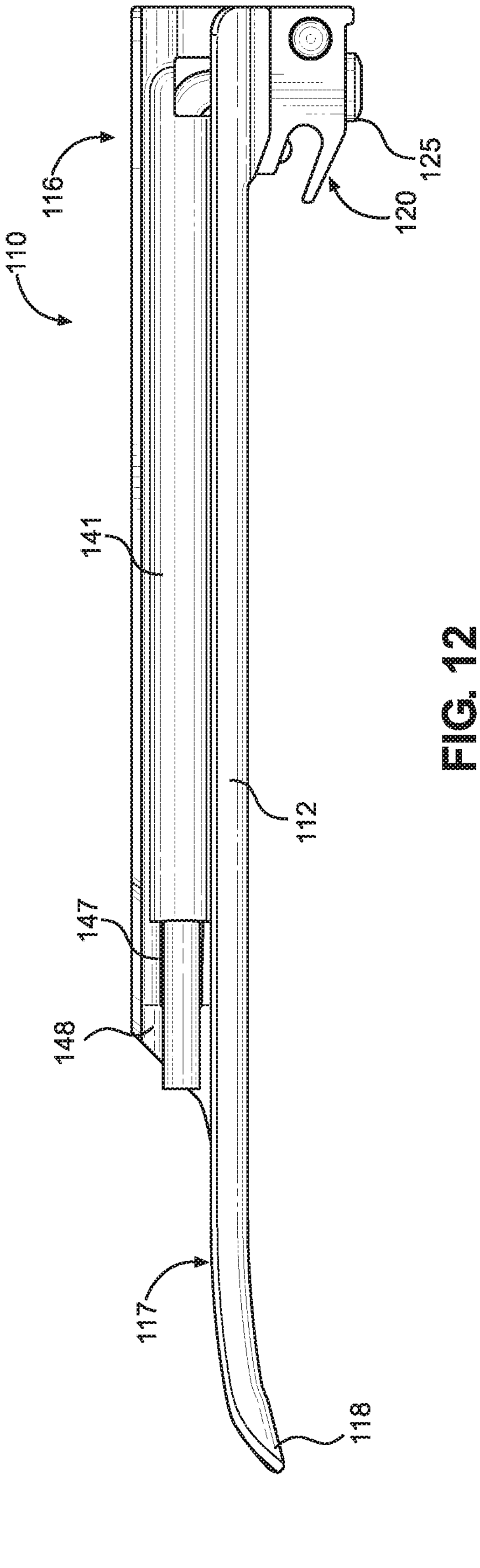
FIG. 12 is a right-side elevation view illustrating a laryngoscope blade in accordance with another implementation of the present disclosure.
Figure 13:
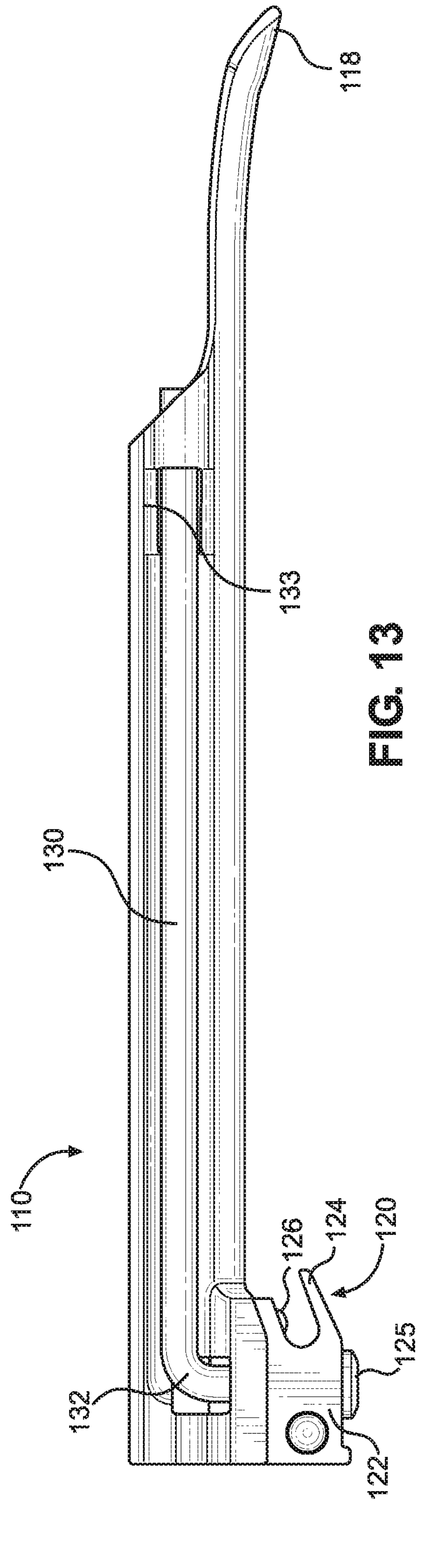
FIG. 13 is a left side elevation view illustrating the laryngoscope blade of FIG. 12.
Figure 15:
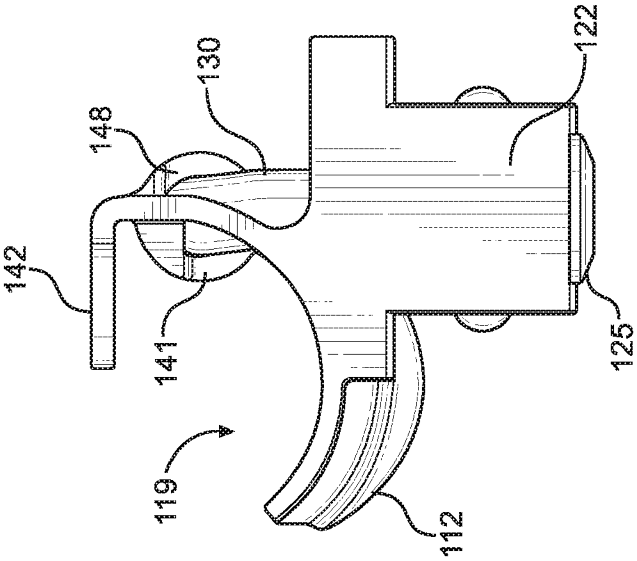
FIG. 15 is a rear elevation view illustrating the laryngoscope blade of FIG. 12.
Figure 14:
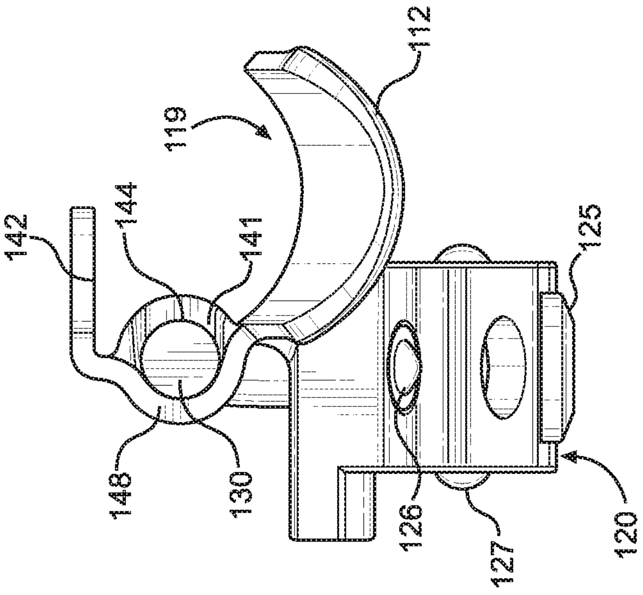
FIG. 14 is a front elevation view illustrating the laryngoscope blade of FIG. 12.

The connector base 20 includes a rear heel portion 22 and a front claw portion 24 configured to detachably engage a portion of the laryngoscope handle. The light guide 30 may be bent to fit within the housing 40 and extends from the distal region 17 of the blade 10 to the proximal region 16 of the blade, and more particularly, to a bottom of the heel portion 22. The proximal end 32 of the light guide 30 is bent downwardly through a vertically extending slot 23 formed in the heel portion 22. An annular elastomeric fastener 25, such as a resilient collar which may be made from PVC or other suitable elastomeric material, fittingly and securely receives the proximal end 32 of the light guide 30 therein. The fastener 25 is securely received in the vertically extending slot in the heel portion 22 and includes a lip **25*a* that extends from the bottom surface of the heel portion 22 so that the proximal end 32 of the light guide 30 likewise extends from the bottom surface of the heel portion 22, as illustrated in FIG. 11. When the laryngoscope blade 10 is attached to the handle in the operative L-shaped position, the elastomeric lip 25***a* of the fastener 25 is correspondingly squeezed therebetween thereby reducing the tolerance between the laryngoscope blade and the handle to ensure a stable connection during use. In some aspects, the lip portion 25*a* of the fastener 25 may have a frustoconical shape to help center the connector base 20 on the handle.

The claw portion 24 defines an inclined slot configured to receive a cross pin of the laryngoscope handle when assembled, i.e., by pivotally mounting the blade 10 to a handle. A first spring loaded poppet 26 is disposed in the heel portion 22 and is open to the slot in order to resiliently engage a top of the cross pin to assist in holding the assembly together. A pair of second spring loaded poppets 27 is disposed in the heel portion 22 and extend laterally from respective sides of the heel portion to engage mating detents in the handle to assist in holding the assembly together. The heel portion 22 further includes a protrusion configured to block light emitted from the light source located in the handle from shining into the practitioner's eyes when the blade is operatively connected to the handle. Stated another way, the protrusion on the heel portion 22 is operable to close a gap between the handle and the blade to prevent glare from the light source from affecting the practitioner's vision during use of the laryngoscope on a patient.

FIGS. 12 to 20 show another implementation of a laryngoscope blade 100 according to the present disclosure. The laryngoscope blade 100 is configured to be inserted into a patient's airway passage. The laryngoscope blade 100 is further configured to be removably attached to a laryngoscope handle to form an operative generally L-shaped configuration for assisting intubation.

In particular, FIGS. 12 to 20 illustrate an implementation of a generally straight type laryngoscope blade 100 according to the present disclosure. The laryngoscope blade 100 may be made from metal, plastic, or a combination thereof. For instance, the blade 100 may be made from austenitic stainless steel, or may be molded from a biocompatible plastic. Further, the laryngoscope blade 100 may be a single-use design to prevent potential contamination between uses. The laryngoscope blade 100 includes a laryngoscope spatula 112 having a concave top surface 113 and a convex bottom surface 114. The laryngoscope spatula 112 further has a longitudinal centerline 115 and a proximal region 116 and a distal region 117 correspondingly adjacent to and remote from the laryngoscope handle in the operative generally L-shaped configuration. The distal region 117 of the spatula 112 may be bent downwardly and terminates in a tip 118 to prevent or minimize trauma to a patient during insertion into the patient's airway passage.

The laryngoscope blade 100 also includes an illumination arrangement for providing illumination at the distal region 117 of the spatula 112 when in the operative configuration. The illumination arrangement includes a handle mounted illumination source, such as a bulb, and a blade mounted light guide 130, such as a polymer-based flexible carrier tube having a fiber optic cable, or a bundle of fiber optic cables, disposed therein for transmitting the illumination light from the illumination source to the distal region 117 of the spatula. More specifically, the light guide 130 includes a proximal end 132 configured to communicate with the illumination source, and a distal end 133 configured to illuminate the distal region 117 of the spatula 112 to assist visual inspection of the larynx or esophagus of the patient. It should be appreciated that various types of light sources may be incorporated within the lighting system. For example, the light source may be mounted within the handle and may include a light emitting diode (LED), a halogen bulb, a krypton bulb, and/or a xenon bulb, among others. In some implementations, the light source may be located in the laryngoscope blade. A power source, such as a battery, for powering the illumination source may be provided within the handle.

The proximal region 116 of the laryngoscope blade 110 includes a connector base 120 having a snap fit arrangement for detachably engaging the laryngoscope blade 110 with the laryngoscope handle. The laryngoscope handle may be reusable and includes a grippable housing which is configured to retain the source of electrical power, such as the battery, and the source of light, such as the bulb. The light and power sources are configured to be actuated upon contact of a portion of the laryngoscope blade with a conductor on a securable mounting end at the upper end of the handle surrounding the bulb.

A light guide housing 140 is connected to the spatula 112. In particular, the light guide housing 140 has a sidewall 141 extending from a longitudinal edge of the spatula 112. The sidewall 141 defines a semi-circular cross-sectional channel 144 configured to stably receive and retain a portion of the light guide 130 therein. Specifically, the sidewall 141 has a concave surface which forms the channel that the light guide 130 is received in. A planar top wall 142 extends laterally from an edge of the side wall 141 and in a direction over a portion of the spatula 112, thus forming a generally flat flange. Biocompatible adhesive may also be applied between the light guide 130 and the semi-circular channel 144 to further ensure the light guide is securely retained in place. A convex portion of the side wall 141 of the housing 140 and the concave top surface 113 of the spatula 112 also cooperate to form a longitudinal channel 119 configured to enable a practitioner to see along the length of the blade and thus into a patient's larynx, and also to provide a passage for intubation of an endotracheal tube.

Figure 16:
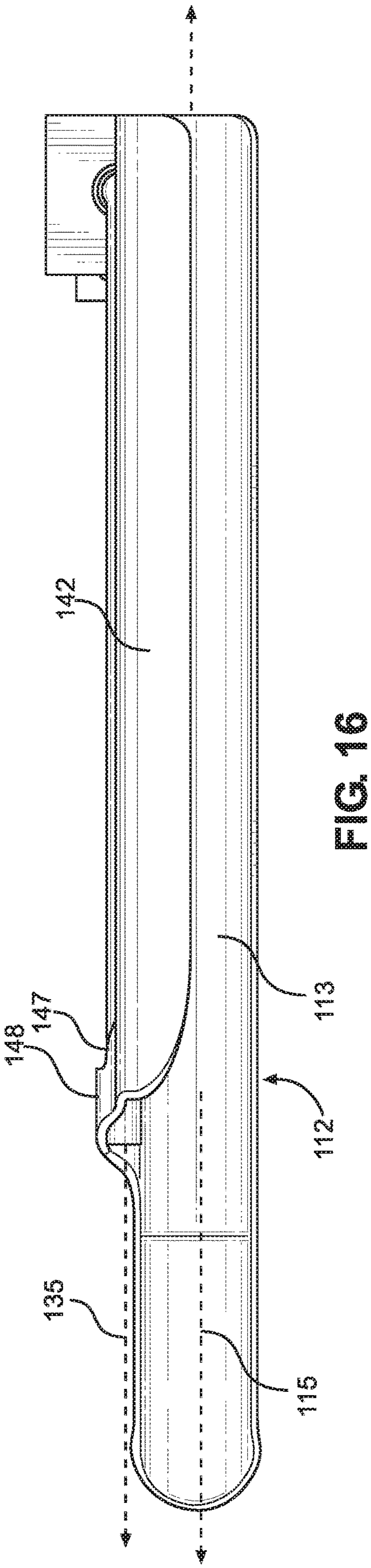
FIG. 16 is a top plan view illustrating the laryngoscope blade of FIG. 12.
Figure 17:
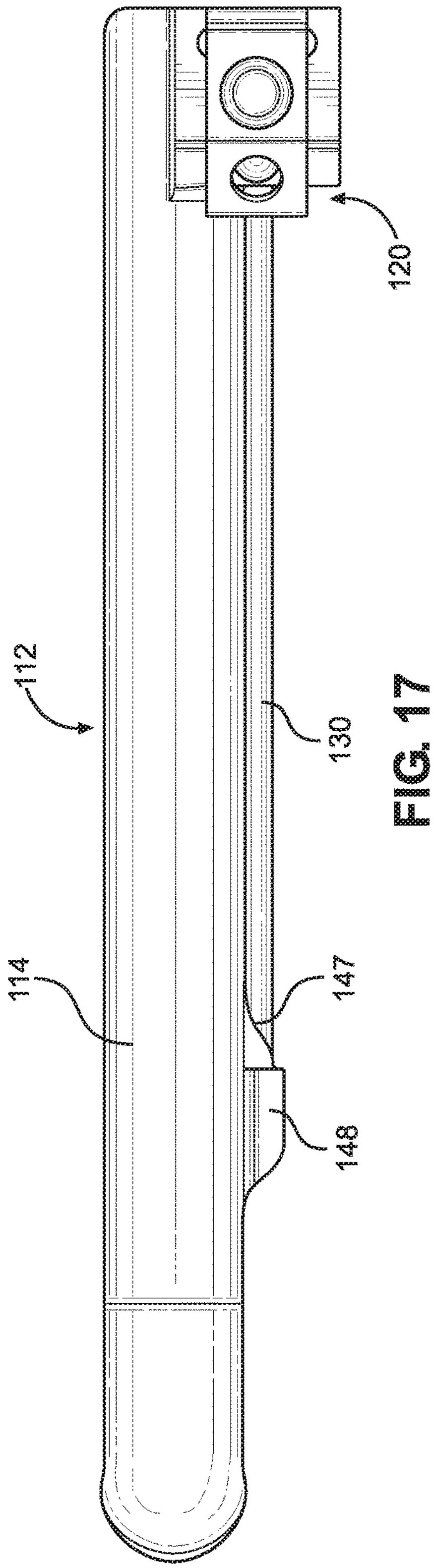
FIG. 17 is a bottom plan view illustrating the laryngoscope blade of FIG. 12.
Figure 18:
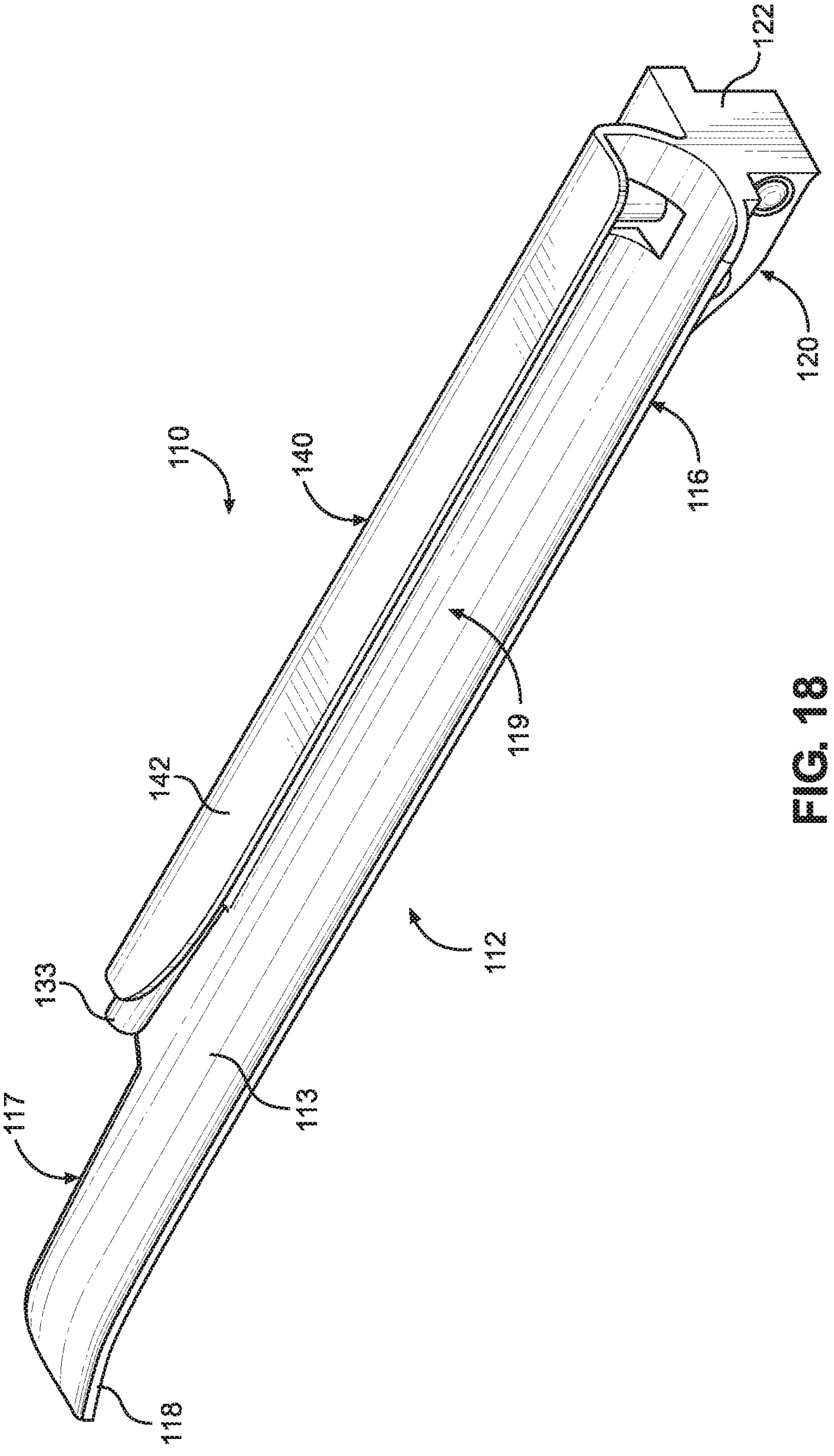
FIG. 18 is a rear perspective view illustrating the laryngoscope blade of FIG. 12.
Figure 19:
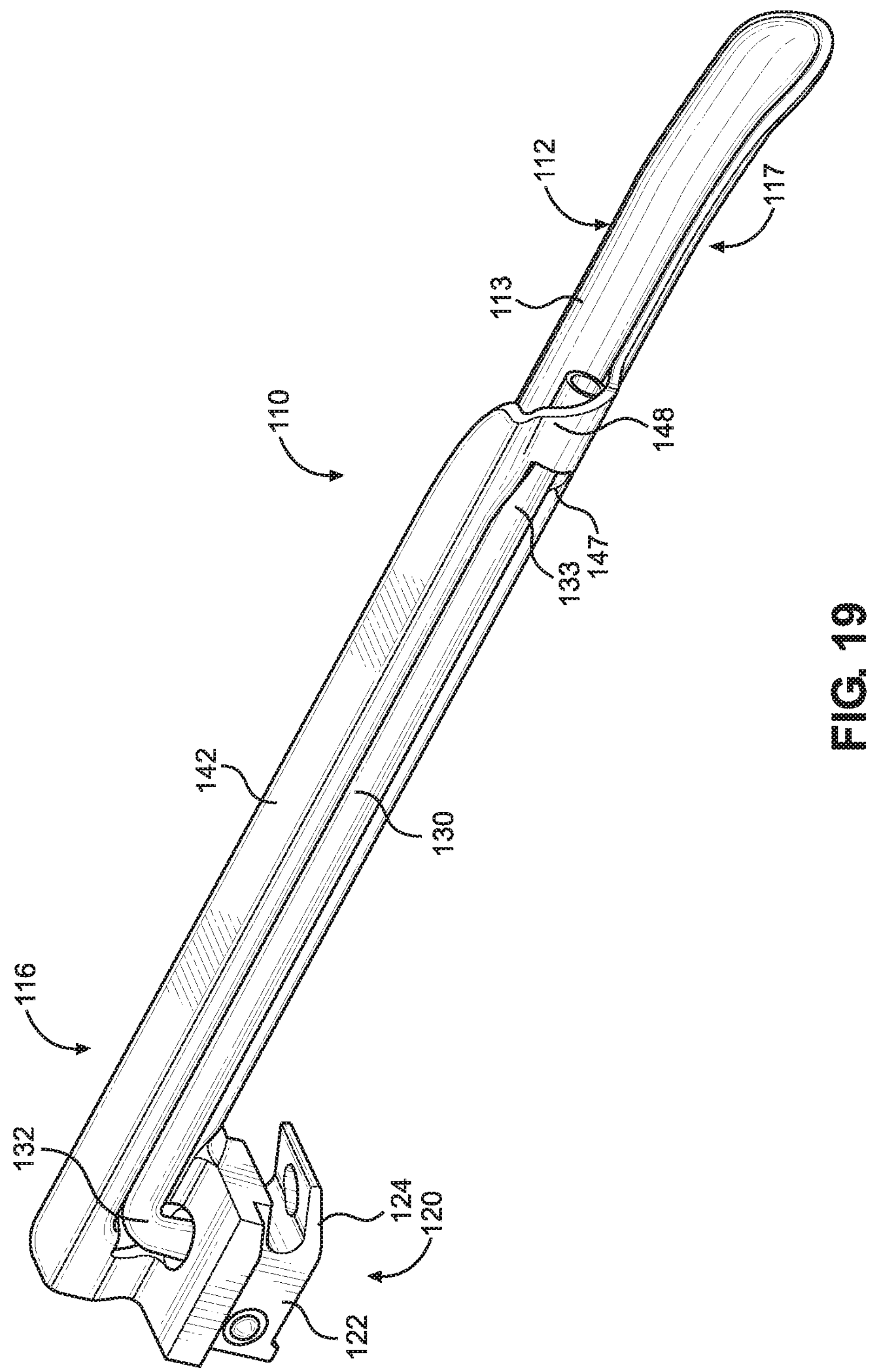
FIG. 19 is a front perspective view illustrating the laryngoscope blade of FIG. 12.

The light guide housing 140 further includes a retaining wall 148 extending from the spatula 112 at the distal region 117 and is connected to the top wall 142. Similar to the side wall 141, the retaining wall 148 has a semi-circular cross section configured to receive and retain a distal end of the light guide 130. In particular, a concave portion of the retaining wall 148 faces in an opposite direction relative to the direction that the concave portion of the side wall 141 faces. An outlet opening 147 disposed between the oppositely oriented side wall 141 and retainer wall 148 is arranged such that the distal end 133 of the light guide 130 can emerge therethrough and be oriented to illuminate straight toward the distal region 117 of the spatula 112, and more particularly, to extend straight toward the blade tip 118. Specifically, a longitudinal axis 135 of the light guide 130 at its distal end 133 is substantially parallel to the longitudinal centerline 115 of the laryngoscope spatula 112 in order illuminate a region directly in front of it, as depicted in FIG. 16. Thus, the complimentary channels or grooves formed by the oppositely oriented concave portions of the side wall 141 and the retainer wall 148 assist with pointing the distal end of the light guide 130 straight ahead along a longitudinal length of the blade during a procedure. Accordingly, when the laryngoscope 110 is in use, it is thus possible to illuminate the oropharyngeal space during laryngoscopy or also during an intubation procedure. Further, the light guide 130 is centered relative to a lengthwise direction of the connector base 120 such that the light guide does not laterally bend to conform with a surface of the blade. As a result, the intensity of light emitted from the distal end of the light guide 30 is not degraded. Further, this arrangement provides a better field of view for the practitioner over conventional light guides that laterally bend toward a direction across a surface of the blade and which therefore obscure the practitioner's field of view.

Figure 20:
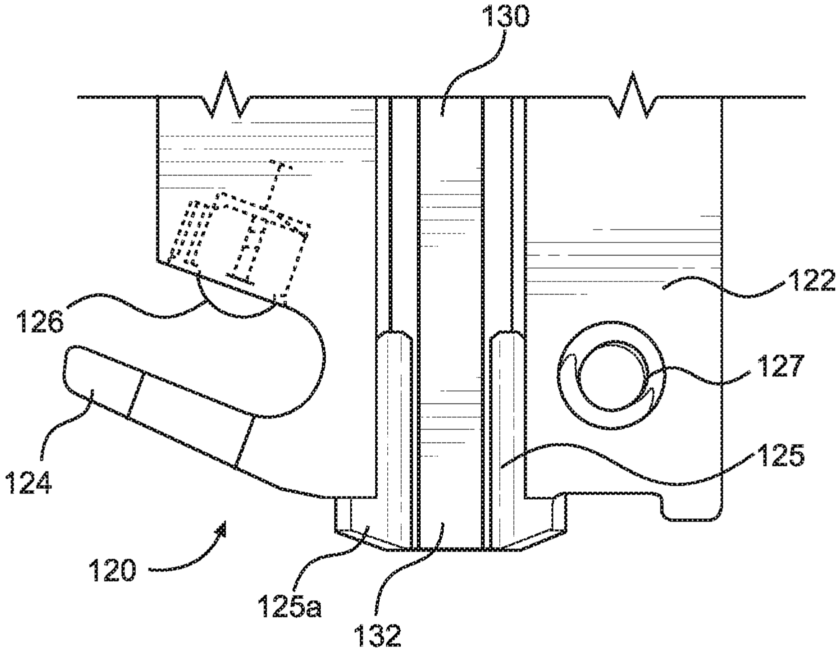
FIG. 20 is a partial cross-sectional view of a connector base of the laryngoscope blade of FIG. 12.

The connector base 120 includes a rear heel portion 122 and a front claw portion 124 configured to detachably engage a portion of the laryngoscope handle. The light guide 130 may be bent to fit within the housing 140 and extends from the distal region 117 of the blade 110 to the proximal region 116 of the blade, and more particularly, to a bottom of the heel portion 122. The proximal end 132 of the light guide 130 is bent downwardly through a vertically extending slot 123 formed in the heel portion 122. An annular elastomeric fastener 125, such as a resilient collar which may be made from PVC or other suitable elastomeric material, fittingly and securely receives the proximal end 132 of the light guide 130 therein. As shown in FIG. 20, the fastener 125 is securely received in the vertically extending slot in the heel portion 122 and includes a lip 125*a* that extends from the bottom surface of the heel portion 122 so that the proximal end 132 of the light guide 130 likewise extends from the bottom surface of the heel portion 122. When the laryngoscope blade 110 is attached to the handle in the operative L-shaped position, the elastomeric lip 125*a* of the fastener 125 is correspondingly squeezed therebetween thereby reducing the tolerance between the laryngoscope blade and the handle to ensure a stable connection during use. In some aspects, the lip portion 125*a* of the fastener 125 may have a frustoconical shape to help center the connector base 120 on the handle.

The claw portion 124 defines an inclined slot configured to receive a cross pin of the laryngoscope handle when assembled, i.e., by pivotally mounting the blade 110 to a handle. A first spring loaded poppet 126 is disposed in the heel portion 122 and is open to the slot in order to resiliently engage a top of the cross pin to assist in holding the assembly together. A pair of second spring loaded poppets 127 is disposed in the heel portion 122 and extend laterally from respective sides of the heel portion to engage mating detents in the handle to assist in holding the assembly together. The heel portion 122 further includes a protrusion configured to block light emitted from the light source located in the handle from shining into the practitioner's eyes when the blade is operatively connected to the handle. Stated another way, the protrusion on the heel portion 122 is operable to close a gap between the handle and the blade to prevent glare from the light source from affecting the practitioner's vision during use of the laryngoscope on a patient.

Furthermore, each of the implementations of the laryngoscope blade discussed herein may comprise a zinc alloy and a powder coating, and may be designed for a single use, or one-time use.

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure. For instance, it should be clearly understood that the particular laryngoscope blades illustrated in the drawings are only examples of a considerable number of different shaped blades which may be for used in various different circumstances, and thus the present disclosure extends to the provision of all forms of laryngoscope blades and not only to those which are illustrated.

What is claimed is:

1. A laryngoscope blade configured to be inserted into a patient's airway, the laryngoscope blade comprising:
- a spatula having a top surface, a proximal region, a distal region, and a longitudinal centerline extending from the proximal region to the distal region;
- a connector base provided at the proximal region of the spatula and configured to removably couple the laryngoscope blade to a laryngoscope handle;
- a light guide having a first end and a second end, the first end attached to the connector base by a resilient fastener, and the second end defining a distal end portion configured to illuminate the patient's airway; and
- a light guide housing adjacent the top surface of the spatula, the light guide housing having:
  - a side wall extending from the top surface of the spatula and defining a space configured to receive a portion of the light guide; and
  - an outlet opening and a retainer wall at the distal region of the spatula, wherein both the outlet opening and the retainer wall are configured to position the distal end portion of the light guide to extend straight toward a tip of the spatula; and
- the distal end portion of the light guide having a longitudinal axis oriented parallel to the longitudinal centerline of the spatula and laterally offset from the longitudinal centerline of the spatula such that the distal end portion of the light guide extends straight toward the distal region of the spatula in a direction parallel to, and laterally offset from, the longitudinal centerline of the spatula, and such that light emitted from the distal end portion of the light guide is oriented directly toward the tip of the spatula.

2. The laryngoscope blade of claim 1, wherein the light guide housing has a stepped configuration including the side wall extending generally vertically from the top surface of the spatula, and a top wall extending laterally from an edge of the side wall.

3. The laryngoscope blade of claim 2, wherein the side wall, a first portion of the top wall, and a portion of the top surface of the spatula cooperate to define a cavity configured to receive and retain a portion of the light guide in a secure position.

4. The laryngoscope blade of claim 3, further comprising a cover removably attached to the light guide housing and configured to seal the cavity for protecting the portion of the light guide retained therein.

5. The laryngoscope blade of claim 4, wherein the cover is configured to be removably snap-fitted onto a portion of the laryngoscope blade to prevent access to the portion of the light guide retained within the light guide housing.

6. The laryngoscope blade of claim 4, wherein the cover includes snap-fit lugs configured to fit in and engage corresponding mounting holes located within the cavity.

7. The laryngoscope blade of claim 4, wherein the cover further includes a flexible tab configured to engage the light guide housing to maintain the cover in a position securely mounted over the cavity.

8. The laryngoscope blade of claim 1, wherein the side wall of the light guide housing and the top surface of the spatula cooperate to form a longitudinal channel configured to enable a practitioner to see along the length of the laryngoscope blade and into a patient's larynx, and also to provide a passage for intubation of an endotracheal tube.

9. The laryngoscope blade of claim 8, wherein the light guide housing further includes an end wall comprising the outlet opening further defining a light guide passage through which the distal end portion of the light guide extends for providing illumination to the distal region of the spatula.

10. The laryngoscope blade of claim 9, wherein the retainer wall extends from the top surface of the spatula at the distal region and is connected to both the end wall and a portion of a top wall.

11. The laryngoscope blade of claim 10, wherein the end wall, the outlet opening, and the retainer wall are configured to position the distal end portion of the light guide to extend straight toward the distal region of the spatula in a direction parallel to the longitudinal centerline of the spatula in order to illuminate an oropharyngeal space during laryngoscopy or during an intubation procedure.

12. The laryngoscope blade of claim 1, wherein the side wall extends from a longitudinal edge of the spatula and defines a semi-circular cross-sectional channel configured to stably receive and retain a portion of the light guide therein.

13. The laryngoscope blade of claim 12, wherein the retainer wall extends from the spatula at the distal region and has a semi-circular cross section configured to receive and retain the distal end portion of the light guide.

14. The laryngoscope blade of claim 13, wherein the outlet opening is disposed between the side wall and the retainer wall and is arranged such that the distal end portion of the light guide extends therethrough and is oriented to illuminate the distal region of the spatula such that a longitudinal axis of the distal end of the light guide is substantially parallel to the longitudinal centerline of the laryngoscope spatula.

15. The laryngoscope blade of claim 1, wherein the connector base includes a rear heel portion and a front claw portion configured to detachably engage a portion of the laryngoscope handle.

16. The laryngoscope blade of claim 15, wherein the light guide is configured to fit within the light guide housing and extends from the distal region of the spatula to the proximal region of the spatula and to a bottom of the heel portion.

17. The laryngoscope blade of claim 16, wherein the fastener is configured to fittingly and securely receive the first end of the light guide therein.

18. The laryngoscope blade of claim 17, wherein the fastener includes a lip that extends from a bottom surface of the heel portion so that the first end of the light guide likewise extends from the bottom surface of the heel portion.

19. The laryngoscope blade of claim 18, wherein the lip of the fastener has a frustoconical shape.

20. The laryngoscope blade of claim 1, further comprising the retainer wall extending from the top surface of the spatula and configured to retain the distal end portion of the light guide, the retainer wall being distal of the side wall and transversely spaced apart from the side wall such that a first distance between the side wall and the longitudinal centerline of the spatula is less than a second distance between the retainer wall and the longitudinal centerline of the spatula.

* * * * *